United States Patent [19]

Hurd

[11] Patent Number: 4,670,119

[45] Date of Patent: Jun. 2, 1987

[54] ISOELECTRIC FOCUSING DEVICE AND PROCESS

[76] Inventor: Stanley M. Hurd, 30 Hawthorne Ave., Hamden, Conn. 06517

[21] Appl. No.: 791,605

[22] Filed: Oct. 25, 1985

[51] Int. Cl.$^4$ .................. G01N 27/26; G01N 27/28
[52] U.S. Cl. .................................... 204/183.2; 204/301
[58] Field of Search ............... 204/299 R, 301, 183.2, 204/183.1, 182.4, 182.9

[56] References Cited

U.S. PATENT DOCUMENTS

| | | | |
|---|---|---|---|
| 3,355,375 | 11/1967 | Badgley | 204/183.2 X |
| 3,758,395 | 9/1973 | Strickler | 204/183.2 |
| 3,915,839 | 10/1975 | Rilbe et al. | 204/299 R |
| 4,315,812 | 2/1982 | Karlson | 204/183.2 X |
| 4,401,538 | 8/1983 | Hausfeld | 204/183.2 X |

Primary Examiner—Donald R. Valentine
Attorney, Agent, or Firm—Bachman & LaPointe

[57] ABSTRACT

An isoelectric focusing technique and apparatus is described in which a steady-state pH gradient is established by the use of a series of parallel electrodes which border the focusing chamber and which may be clamped at varying voltages independently of one another. By maintaining appropriate voltages along with length of the chamber, the ionic species present in the buffer solution will be concentrated at either the anode or cathode end, depending on their charge, and the charge imbalance resulting from this concentration effect will cause the dissociation of water with the concommitant establishment of a pH gradient. By varying the intensity and shape of the voltage gradient, a wide range of pH gradients, and median values for these gradients, may be selected. Further, the gradient may be altered at will during the isoelectric focusing run without disturbing the components being resolved, allowing maximum resolution of a number of components from one run.

18 Claims, 5 Drawing Figures

ISOELECTRIC FOCUSING DEVICE AND PROCESS

BACKGROUND OF THE INVENTION

This invention deals with a biochemical separation technique based on the principle of isoelectric focusing. This is an electrokinetic technique which takes advantage of the fact that many biochemical components, such as proteins, viruses, cells and cellular organelles, exhibit amphoteric qualities.

An amphoteric compound is one which has a number of charged, or potentially charged, acidic and basic moieties in its structure. The number of these acidic and basic moieties which will be charged at any time is dependent on the pH of the surrounding media, and there exists a certain pH at which the number of oppositely charged moieties will be exactly equal, making the net charge of the compound zero. This is called the isoelectric point, or pI. When an amphoteric compund is placed in a pH gradient and an electric potential is applied to it, it will migrate through the pH gradient until it reaches the point at which its net charge is zero. This technique of "focusing" an amphoteric compound at its pI has been in common laboratory use on an analytical scale for the last decade. Since different amphoteric compounds have different isoelectric points, a mixture of a large number of such compounds can be resolved into its component parts in one step, making this a powerful and popular technique.

A number of procedures and devices have been introduced to utilize the principle of isoelectric focusing in biochemical separations (for a complete discussion see P. G. Righetti and J. W. Drysdale, *Laboratory Techniques in Biochemistry and Molecular Biology*, T. S. Work and E. Work, eds., North Holland Publishing Company, Amsterdam, 1976, Vol. 5 and P. G. Righetti, ibid., 1983, Vol. 11).

One of the most common techniques involves the use of compounds known as carrier ampholytes to establish the pH gradient. These ampholytes are small, amphoteric buffer compounds which have their maximum buffering capacity at or near their pI. Therefore, when a mixture of them is placed in an electric field, they migrate to their isoelectric points with the various different types stacking perpendicular to the field, thereby establishing a pH gradient along the field.

There are number of disadvantages to the use of this procedure, most of which arise from the limitations of the ampholytes themselves. The first of these disadvantages involves a phenomenon known as cathodic drift. Briefly, the ampholytes tend to drift slowly in the direction of the cathode, causing the pH gradient to drift as well. This results in the focused proteins moving along with the gradient and losing resolution due to convection and mixing.

Also, the commonly available commercial ampholytes can produce only restricted pH gradients, typically with a range of 1-7 pH units. Since the resolution of the system is inversely proportional to the steepness of the gradient, the narrower the pH range the higher the resolution. It would therefore be desirable to have the ability to produce gradients with ranges significantly less than 1 pH unit.

The ampholytes can complex with the compounds being separated, causing anomalous bands at the pI of the complex rather than the true pI of the compound. It is therefore possible to get several different bands of the same compound, depending on the number of ampholytes with which it has complexed. This can seriously complicate separations in both analytical and preparative applications.

Often, especially in the case of preparative protein separations, the ampholytes must be removed from the purified components by subsequent steps because they interfere with several commonly-used procedures for the assay of peptides. This subsequent separation can be particularly difficult in the case of the short polypeptides, since their molecular weight and charge distribution is often very similar to that of the ampholytes which co-purify with them.

The ampholytes are relatively expensive, which tends to limit their practicality in preparative-scale applications.

Finally, once the pH gradient has been established there is no practical way of changing it during the run. This means that several different attempts are often necessary before the optimum conditions for the separation of a given compound are achieved. Even then, if there is more than one compound of interest to be purified from a mixture it is unlikely that the optimal conditions for one will also be optimal for the others. This often means that only one compound of a mixture can be adequately resolved by a given focusing run. Since a run can require up to three days to complete, this can become a serious drawback.

There have been numerous methods proposed for the formation of pH gradients without the use of carrier ampholytes. In one such method a step-gradient was produced by using membrane-bound compartments containing media at different pH values (A. J. P. Martin and F. Hampson, *Journal of Chromatography*, Vol. 159, p. 101, 1978). The membranes allowed passage of the material to be focused while maintaining the pH gradient. However, electroendosmotic flows carrying the buffer species along with the focusing material tended to disrupt the pH gradient, thereby lowering resolution. Also, the resolution was relatively low in any case due to the discontinuous nature of the gradient.

Another system involved the use of two equal and opposite streams of buffer at different pH values to establish a pH gradient in a convection-free zone bounded by the two streams (H. Rilbe, *Journal of Chromatography*, Vol. 159, p. 193, 1978 and U.S. Pat. No. 4,217,193). However, the pH gradient formed by this method is insufficiently stable for high-resolution focusing.

Yet another method has been proposed which involves the use of ion-selective membranes in conjunction with a chamber with non-parallel sides to produce a pH gradient (A. D. Hausfeld, U.S. Pat. No. 4,401,538). In this system, the non-parallel walls of the chamber cause the electric field lines generated by the anode and cathode means at either end of the chamber to assume different densities at different portions of the chamber. The focusing takes place in a secondary chamber having parallel walls which is nested inside the irregularly shaped chamber. These walls are constructed of ion-selective membranes which will pass ions of only one charge type. The ions of the solution will move at different rates in different portions of the chamber owing to the different field densities they experience. Those ions which are constrained inside the membrane compartment will not maintain equal distribution with regard to their counter-ions which can move freely through the membranes. This results in a charge imbalance which is balanced by the dissociation of water, creating a pH gradient.

The two main drawbacks to this procedure are: (1) it requires a power supply with very large current capacity, since most of the current flows through the outer chamber rather than through the focusing chamber. This necessitates special precautions to dissipate the additional heat caused by these large current flows. And (2), it shares the lack of flexibility in choice of gradients with the ampholyte technique (to change the gradient it is necessary to change the configuration of the chamber).

It is therefore an object of the present invention to provide an improved method for isoelectric focusing. A specific object of the present invention is to establish a pH gradient without the use of carrier ampholytes.

Another object of the present invention is to provide a method for establishing pH gradients with a range significantly less than 1 pH unit.

It is another object of the present invention to provide a means of altering the shape, range and median value of a pH gradient during the focusing run.

Still another object of the present invention is to provide a method of and apparatus for isoelectric focusing which will be compatible with high-capacity and continuous flow-through preparative applications.

It is also an object of the present invention to provide a method of and apparatus for isoelectric focusing in which the operator can select from a wide range of buffer solutions in which the focusing may take place.

SUMMARY OF THE INVENTION

In accordance with the present invention the foregoing objects and advantages can be readily obtained.

Thus, the present invention resides in an apparatus for establishing an ion concentration gradient in an electrolyte containing two or more types of ions which comprises: an electrolyte; a focusing chamber containing said electrolyte; anode and cathode means disposed in fluid communication with said electrolyte for establishing an electric field within electrolyte contained in said focusing chamber; a plurality of electrode pairs bordering said focusing chamber to establish a non-linear voltage gradient in said focusing chamber, whereby the ionic species present in said electrolyte will be concentrated at either the anode or cathode end giving rise to a steady-state pH gradient in said focusing chamber.

In addition, the present invention resides in a process for establishing an ion concentration gradient in an electrolyte solution containing two or more types of ions which comprises: confining an electrolyte solution in a focusing chamber having an anode end and a cathode end; establishing an electric current through said solution; and providing a plurality of electrode pairs bordering said focusing chamber and applying a non-linear voltage gradient to the electrode pairs along the length of the focusing chamber, whereby the ionic species present in said electrolyte will be concentrated at either the anode or cathode end thereby establishing a steady-state pH gradient in said focusing chamber.

In accordance with the present invention an isoelectric focusing technique and apparatus is provided which employs an isoelectric focusing chamber in which a series of electrodes along the walls of the chamber are held at different voltages such that a uniform, non-linear voltage gradient is established along the length of the focusing chamber. When the voltages are applied in the presence of an electrolytic solution, the non-linear voltage gradient will cause the electrolytes to move at different rates in different portions of the focusing chamber. The charge imbalances resulting from these differing rates of flux are balanced by the dissociation of water, thereby establishing a pH gradient.

In a preferred embodiment, the focusing chamber would be constructed to form a narrow rectangular space having a series of parallel electrodes running the length of two facing walls of the focusing chamber. The electrodes on each wall would be paired such that the plane formed between them would be orthogonal to the long axis of the focusing chamber. In a preferred embodiment, the electrode pairs would be equally spaced along the length of the focusing chamber so that the actual voltage gradient inside the focusing chamber accurately reflects the applied voltage gradient. Each two paired electrodes would be clamped at the same voltage so that there would be no lines of force between them.

In such a preferred embodiment, the lines of electric force would have a net component parallel to the long axis of the focusing chamber, and the field densities would be quite uniform in any given plane taken orthogonally to the long axis. This in turn provides the uniform pH gradient necessary for successful isoelectric focusing.

The charge imbalances which give rise to the pH gradient are the result of the accumulation of either anions or cations caused by their different rates of flux in the differing regions of the focusing chamber. For example, if the electrodes were clamped at voltages which decreased exponentially from the anode end of the chamber to the cathode end of the chamber, the cations at the anode end of the chamber would move very quickly toward the cathode end, while the cations at the cathode end would be moving relatively slowly. This is because the potential difference between adjacent electrode pairs at the anode end is large relative to the difference at the cathode end, by virtue of the exponential voltage gradient. In this situation, a net positive charge imbalance would result at the cathode end of the chamber, which would be offset by hydroxide ions supplied by the electrolytic dissociation of water. The pH gradient in this case would increase from anode to cathode, as is required for isoelectric focusing.

Inasmuch as this is a steady-state rather than equilibrium process, it will be understood that a sink and a source of the electrolytes must be provided. Therefore, the focusing chamber is placed in a larger reservoir chamber filled with the the same electrolytic solution. In a preferred embodiment the ends of the focusing chamber are bounded by some material which will allow the free passage of electrolytes but restrict the passage of the macromolecules to be focused. In a preferred embodiment this would be accomplished by placing dialysis membrane over the ends of the focusing chamber in contact with the reservoir solution.

The steepness of the pH gradient can be varied over a very wide range since the steepness of the pH gradient is, in general, a function of the steepness of the voltage gradient. This is due to the fact that the accumulation of ions in one segment is a function of how greatly the voltage gradient in that segment differs from the neighboring segments' gradients. In terms of the potential difference, $\Delta V$, between two points along the long axis of the chamber, $X_1$ and $X_2$, the steepness of the pH gradient will be proportional to the rate of change of $\Delta V/\Delta X$, where $\Delta X = X_2 - X_1$. It is therefore possible to select any given pH range desired by applying the proper voltage gradient to the focusing chamber.

Further, it is possible to control the median value of the selected pH range by the means of electrodes placed in the reservoir chamber, which in a preferred embodiment would be placed at either end of the focusing chamber. The function of these electrodes may be understood by examining their effect in the example given above, in which an exponentially decreasing voltage gradient was used to establish a cation concentration gradient. In this case $\Delta V/\Delta X$ decreases from the anode to the cathode. If the external electrode at the anode end is held at a voltage such that $\Delta V/\Delta X$ between the external electrode and the first electrode inside the focusing chamber is greater than $\Delta V/\Delta X$ between the first and second electrodes, the flux of cations into the initial segment of the focusing chamber will be greater than the flux out of that segment, and the resulting positive charge imbalance will cause an increase in the pH of the initial segment with respect to the external solution. Similarly, by making $\Delta V/\Delta X$ from the external electrode to the first electrode less than $\Delta V/\Delta X$ from the first electrode to the second electrode, the flux of cations into the initial segment would be less than the flux out, resulting in a lower pH in the initial segment with respect to the reservoir solution. Since the exponentially decreasing voltage gradient in the focusing channel will maintain a monotonically increasing pH gradient regardless of the pH of the initial segment, the regulation of the pH of the initial segment controls the median value of the pH gradient throughout the focusing chamber.

By combining these two processes, the steepness of the voltage gradient and the value of the external electrode, it is possible to establish a wide range of pH gradients and median values of these gradients with almost any electrolyte solution. Further, it is possible to alter the pH gradient during an isoelectric focusing run without departing the contents of the focusing chamber, allowing the selection of the gradient or gradients which will maximize the separation of the component or components desired.

BRIEF DESCRIPTION OF THE DRAWINGS

For a fuller understanding of the present invention described herein, reference should be made to the accompanying drawings, wherein.

In the various views, like index numbers refer to like parts.

DETAILED DESCRIPTION

Figure 1:
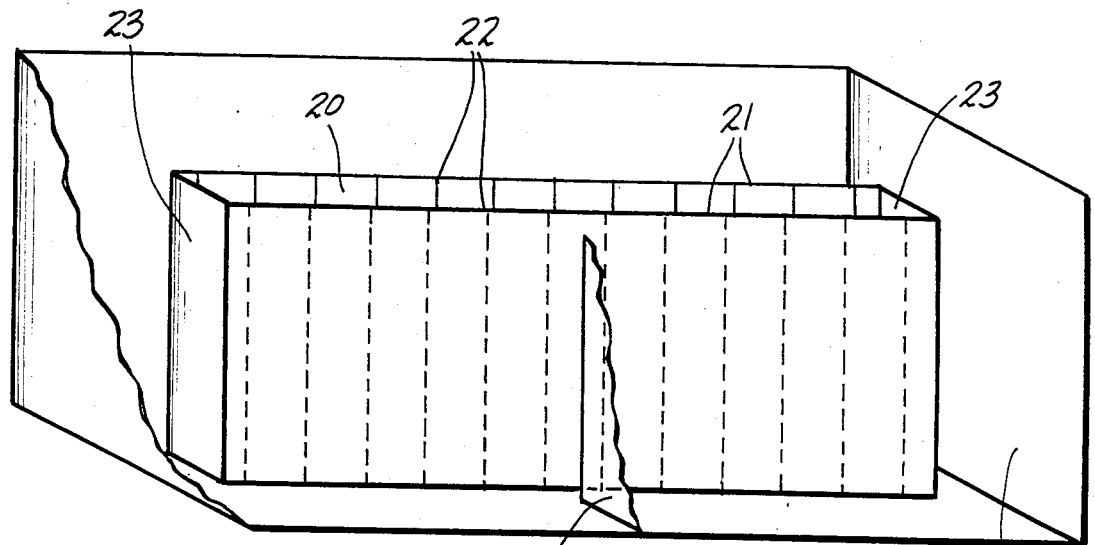
FIG. 1 is a schematic representation of a preferred embodiment, seen obliquely from the top, with the side and front walls of the reservoir chamber removed to show the placement and design of the focusing chamber.

FIG. 1 shows a preferred embodiment of the invention in an oblique view from the top, with the front wall and sides of reservoir chamber 10 cut away to illustrate focusing chamber 20 within the reservoir chamber.

Figure 2:
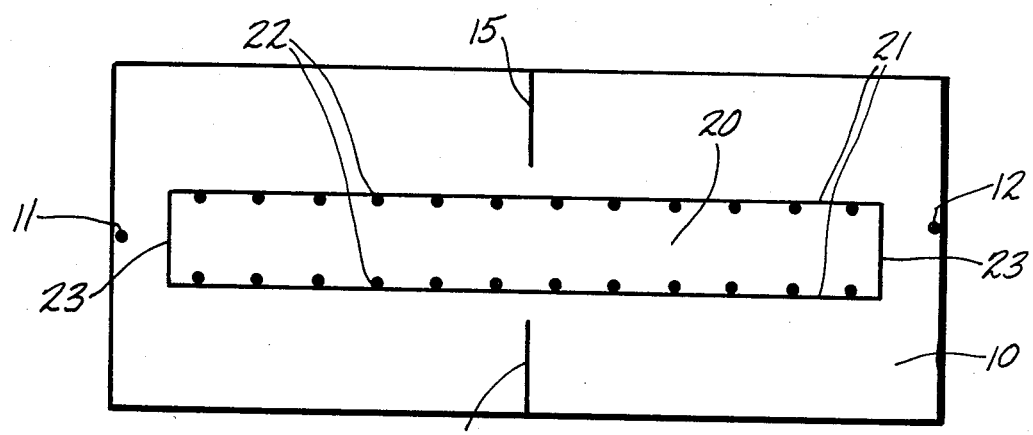
FIG. 2 is a schematic representation of the embodiment of FIG. 1 seen from the top, illustrating the placement of the electrodes.

Focusing chamber 20 is comprised of two side walls 21 constructed of a rigid, inert, insulating material, extending from the bottom of the reservoir chamber 10 to above the level of the electrolyte solution in reservoir chamber 10. Along the inner surface of these walls are positioned a series of electrode pairs, 22, arranged such that the plane formed between the two members of a pair is orthogonal to the long axis of focusing chamber 20. These electrodes may be constructed of conducting materials such as platinum wire or thin, linear graphite films. FIG. 2 shows a top view of the same embodiment illustrating the placement of the electrode pairs. Each electrode pair is electrically connected to a suitable power source to maintain the desired voltage gradient along focusing chamber 20. In this embodiment the electrode pairs are equally spaced along the length of focusing chamber 20, so that a non-linear voltage gradient applid to them would be accurately reflected by the field lines in the focusing chamber. However, it would also be feasible to use a non-linear spacing in conjunction with a linear voltage gradient to achieve a similar result, see, for example, FIG. 5 which shows a non-linear, logarithm spacing.

The ends 23 of focusing chamber 20 are covered with a material which is permeable to the small electrolytes of the reservoir solution, but which is impermeable to the larger amphoteric species to be resolved in the focusing chamber. In a preferred embodiment this material might be dialysis membrane. Focusing chamber 20 is thus in electrical and chemical communication with the reservoir solution. FIG. 2 shows external electrodes 11 and 12, located on the walls of the reservoir chamber 10 opposite to the ends of focusing chamber 20 at the anode and cathode ends of the focusing chamber, respectively. As in electrode pairs 22, these electrodes are of a conducting material such as platinum or graphite, and each is connected to a suitable power source.

In order to reduce convection due to the gases evolved during electrolysis, focusing chamber 20 may be lined with an inert, conductive membrane to prevent disruption of the gradient by said convection. In a preferred embodiment this membrane might be dialysis membrane.

Reservoir chamber 10 is constructed of an inert and non-conductive material. The volume of this chamber must be sufficiently greater than that of focusing chamber 20 that the concentration of electrolytes remains essentially constant during focusing. It shall be supplied with a suitable means of mixing (not shown) so that the anlytes and catholytes produced at the electrodes can be adequately mixed and neutralized, in order to maintain steady-state conditions during the focusing run. It is also supplied with means for reducing the amount of current flowing through reservoir chamber 10 by reducing the cross-sectional area of the reservoir chamber, as by non-conductive baffles 15 which substantially reduce the cross-sectional area of the reservoir chamber. In this embodiment the baffles do not extend completely from the walls of reservoir chamber 10 to the side walls 21 of the focusing chamber. The reason for this is that the buffer solutions in the reservoir chamber 10 serve to dissipate the heat generated in focusing chamber 20 by the electrical currents flowing therein. If the baffles made contact with side walls 21, there would be a reduction of thermal conductivity at the point of contact. This would lead to convection inside focusing chamber 20, tending to disrupt the pH gradient.

In order to establish a steady-state ion gradient, the voltage gradient applied to the electrode pairs along the length of focusing chamber 20 must be non-linear. This may be understood by referring to FIG. 3, which shows a detail of the focusing chamber with three imaginary planes, orthogonal to the long axis of the channel, placed at distances $X_1$, $X_2$, $X_3$, respectively, and defining spaces 1 and 2 as shown. For an exponentially decreasing voltage gradient, the quantity $\Delta V/\Delta X$ would be greater at the plane at $X_1$ than at the plane at $X_2$, which would be greater than $\Delta V/\Delta X$ at $X_3$, and so forth. Therefore, if we consider a population of cations moving along this potential gradient we see that their initial rate of flux at $X_2$ would be greater than at $X_3$. Accordingly, there would be an increase in the cation concentration in volume 2 relative to volume 1. Since the flux is proportional to both the voltage gradient and ionic concentration at any given plane, eventually the rate of flux out of volume 2 would equal that out of volume 1 as the concentration in volume 2 became sufficiently greater than that in volume 1 to offset the difference in $\Delta V/\Delta X$. This steady-state condition would persist as long as the voltage gradient along the focusing chamber and the ion concentration in volume 1 remained constant.

It should also be noted that for any given voltage gradient, the actual steady-state concentration gradient established will depend on the rate of flux of cations into the initial segment of focusing chamber 20. This is due to the fact that the steady-state concentration of ions in any segment of the focusing chamber is dependent on $\Delta V/\Delta X$ across the segment and the rate of flux of the cations into it from the preceding segment.

Figure 3:
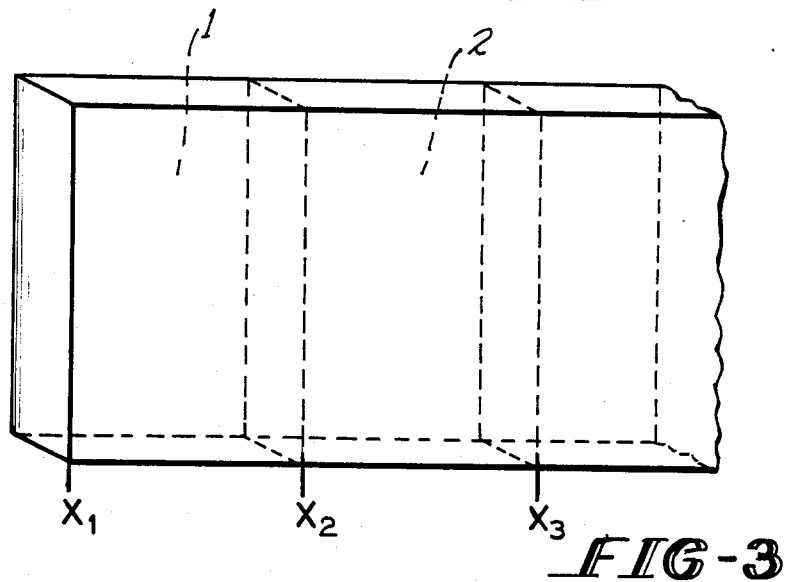
FIG. 3 is a fragmentary schematic representation of the focusing chamber of the embodiment of FIG. 1, in which a portion of the focusing chamber has been divided into two volumes by three hypothetical planes.

If the plane at $X_1$ in FIG. 3 is taken to be the boundary of the first segment of focusing chamber 20, it will be understood that by controlling the flux of cations through this plane it is possible to affect the overall concentration range, and therefore the level of charge imbalances leading to the pH gradient, throughout the length of focusing chamber 20. In other words, the rate of flux through the initial segment of the focusing chamber will determine the median value of the pH gradient to be established. Described qualitatively using the example above, if the initial flux of cations into the first segment (volume 1 of FIG. 3) of the focusing channel is greater than the initial flux through the plane at $X_2$ into volume 2, then at steady-state conditions the average concentration of cations within the focusing chamber will be greater than the concentration of cations in the reservoir chamber. Therefore, since this increase in positive charge will be offset by an increase in hydroxide ion concentration, the median pH inside the focusing chamber will be higher than the pH of the reservoir solution.

It is the role of the external electrodes 11 and 12 to control the flux of ions into focusing chamber 20, and therefore the steady-state concentration of ions at the extreme ends of the focusing chamber. Again taking the example of cations moving through an exponentially decreasing electrical potential, if the quantity $\Delta V/\Delta X$ between external electrode 11 (at the anode end of the focusing chamber) and the first electrode is greater than $\Delta V/\Delta X$ between the first and second electrodes, then the initial flux into the first segment of focusing chamber 20 will be greater than the flux out. Therefore, the concentration of cations in the first segment at steady-state will be greater than the cation concentration of the reservoir solution. This being true, the positive charge imbalance of the first segment would be offset by hydroxide ions, raising the pH of the first segment above the pH of the reservoir solution. Similarly, if the quantity $\Delta V/\Delta X$ between the external electrode and the first electrode in the focusing chamber is less than $\Delta V/\Delta X$ between the first and second electrode of the focusing chamber, this would lead to a lower steady-state cation concentration in the first segment, thus a lower pH than that of the reservoir solution.

Since the slope of the pH gradient, $\Delta pH/\Delta X$, is proportional to the slope of the function $\Delta V/\Delta X$, and is only very weakly dependent on the actual ionic concentrations in the focusing chamber, it will be understood that the slope of the pH gradient will remain relatively unchanged by manipulations of the voltages of the external electrodes. Therefore, it is possible to alter the median value of the pH gradient, by using appropriate voltages at the external electrodes, without significantly changing the slope of the gradient. In other words, one may choose between either steep or shallow gradients, centered on any pH value, simply by selecting the appropriate combination between the voltage gradient in the focusing channel and the voltages of the external electrodes.

Thus far we have limited the discussion to a single ionic species of positive charge. This type of special case can obtain only when a compound exists as a cation or a neutral species. A well-known example of such a compound is TRIS (tris hydroxymethyl aminomethane), which exists as either the cationic acid or the neutral base. But, in most solutions of interest to the biochemist a number of different electrolytes are present, both anions and cations. In these cases, it is necessary to determine whether the anionic or cationic species will dominate in the processes leading to the establishment of the pH gradient. In general, the contribution of each species will be proportional to the quantity (conc $\times \mu$) where conc is the concentration of the species in the starting solution and $\mu$ is its electrophoretic mobility. If this quantity is summed for all anionic species, and again for all cationic species, the greater sum will be that of the dominant species. It has been shown how an exponentially decreasing voltage gradient will produce a concentration gradient of cations. In a similar fashion, a logarithmically decreasing voltage gradient will produce an anionic concentration gradient. It is therefore possible to use this technique with any solution in which the sum of (conc $\times \mu$) for the anioic species is not equal to the sum of (conc $\times \mu$) for all cationic species.

In practice it is not necessary to know beforehand whether anionic or cationic species are dominant. If an exponentially decreasing gradient is applied and the resulting pH gradient increases from the anode end to the cathode end of focusing chamber 20, the dominant species is cationic. If the pH gradient decreases from the anode end to the cathode end, the dominant species is anionic, and a logarithmically decreasing voltage gradient must be applied to produce the pH gradient necessary for isoelectric focusing.

It must be noted that there is another phenomenon which contributes to the pH gradient: the electrolytic dissociation of water. When the applied voltage varies sufficiently from linearity, the electrolytic dissociation of water will take place at the electrode pairs, hydrogen ions forming at anodes and hydroxide ions forming at cathodes. By using a sufficiently non-linear voltage gradient (i.e., one in which the difference in $\Delta V$ between two sets of adjacent electrode pairs, such as $\Delta V_{1,2}$ and $\Delta V_{2,3}$, varies from linearity by more than about 1 V, the voltage necessary to cause the half reception $2H_2O + 2e^- \rightarrow H_2 + 2OH^-$ to proceed, one can in fact establish a steady-state pH gradient in the absence of other ions. However, these types of gradients are more difficult to control, since there are no buffer species present to stabilize the gradients.

This effect will alter the gradients established by the methods discussed above, and should be taken into consideration, especially in that they can give rise to biphasic pH gradients. This occurs when a very non-linear and inverse voltage gradient (e.g. a logarithmically decreasing gradient in a cationic solution) is applied. In this case, the pH gradient will be inverted where the voltage gradient is close enough to linearity that the breakdown of water does not occur, but will be normal where the electrolysis is sufficient to overcome the charge imbalance effect already discussed.

Figure 4:
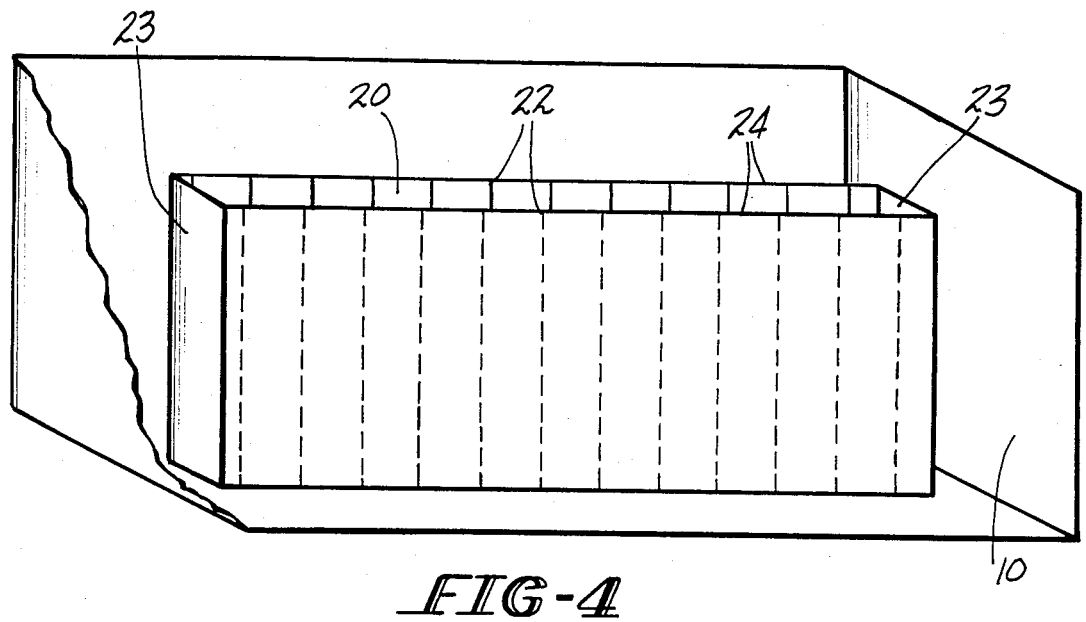
FIG. 4 is a schematic representation of an alternate embodiment similar to that of FIG. 1, in which the walls of the focusing channel are comprised of semi-permeable, ion-selective membranes.

FIG. 4 shows an alternate embodiment, in which the side walls 24 of the focusing chamber are comprised of semi-permeable, ion-selective membranes such as those commonly used in electrodialysis. These membranes have the property of allowing electrolytes of only one charge (i.e., only anions or cations) to pass through them freely. As will be described below, this embodiment has the advantage of allowing the use of virtually any electrolytic solution to establish the desired pH gradient.

In the alternate embodiment of FIG. 4, it is possible to designate either anionic or cationic species as dominant by the use of such ion-selective membranes. The use of these membranes, in place of impermeable side walls 21 as shown in FIG. 1, will allow only species of one charge type to accumulate in the focusing chamber, since those species to which the membrane is permeable will diffue through it back into the reservoir chamber. In this way, species of one charge may be driven to accumulate while species of the other charge will remain nearly constant, at a concentration near or equal to their concentration in the reservoir. In the case of a cation concentration gradient, an anion-selective membrane, such as type 103-PZL-386, produced by Ionics, Inc. of Watertown, Mass., would be used to restrain cations within the focusing chamber, but to allow passage of anionic species. In this embodiment it is not possible to use baffles to reduce the current flowing through the reservoir chamber as was described for the embodiment of FIG. 1. This is because the semi-permeable membrane side walls are electrically conductive, and the excessive variations in electric field densities caused by such baffles would lead to anomalous currents within the focusing chamber.

Figure 5:
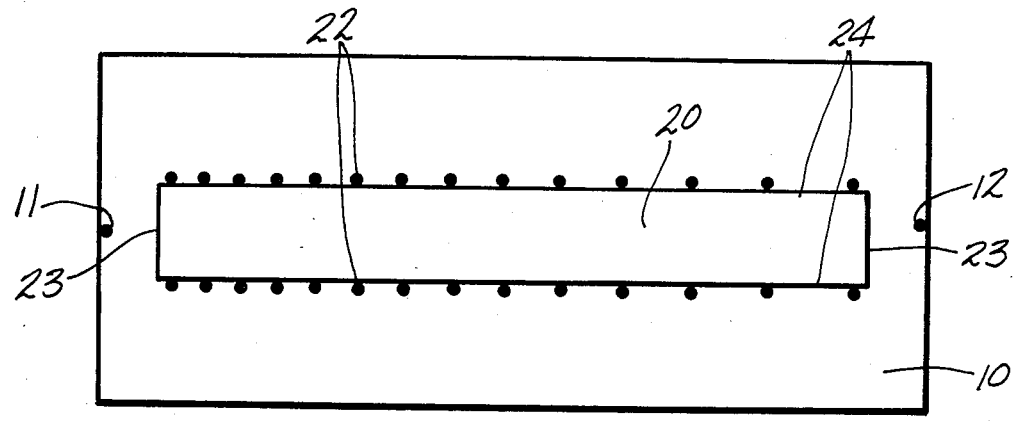
FIG. 5 is a schematic representation of another alternate embodiment, similar to that in FIG. 4, seen in top view to illustrate the placement of the focusing electrodes outside the focusing chamber and wherein the electrode spacing is non-linear, i.e., logarithmic.

In another alternate embodiment, similar to that of FIG. 4, the channel electrode pairs 22 are placed outside the membrane, in contact with the reservoir solution. This embodiment is shown in a top view in FIG. 5, showing the placement of electrode pairs 22. This embodiment has the advantage of using the electric potentials generated by electrode pairs 22 as the driving force to increase the diffusion rate of the ions passing through ion-selective membrane walls 24. This provides a more uniform concentration of the non-dominant species, so that the charge imbalances established by the ions retained in the focusing chamber will be less subject to distortion. However, since the electrical conductance of ion-selective membrane walls 24 will not necessarily be the same as the surrounding electrolyte solution, some distortion of the electric field lines in focusing chamber 20 may result from this embodiment. FIG. 5 also shows non-linear electrode spacing bordering said focusing chamber. The non-linear electrode spacing can of course be used in the other embodiments.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. An apparatus for establishing an ion concentration gradient in an electrolyte containing two or more types of ions which comprises: an electrolyte; a continuous focusing chamber having a long axis containing said electrolyte; anode and cathode mans disposed in fluid communication with said electrolyte for establishing an electric field within electrolyte contained in said focusing chamber; a plurality of parallel, vertically aligned, spaced-apart electrode pairs with the members of each pair situated on opposite sides of said focusing chamber and bordering said focusing chamber such that the plane formed between each pair is orthogonal to the long axis of the focusing chamber to establish a non-linear voltage gradient in said focusing chamber wherein the lines of electric force have a net component parallel to the long axis of the focusing chamber, whereby the ionic species present in said electrolyte will be concentrated at either the anode or cathode end giving rise to a steady-state pH gradient in said focusing chamber proportional to the voltage gradient.

2. An apparatus according to claim 1 wherein the electrode spacing is linear.

3. An apparatus according to claim 1 wherein the electrode spacing is non-linear.

4. An apparatus according to claim 1 including a reservoir chamber wherein said focusing chamber is within said reservoir chamber.

5. An apparatus according to claim 4 wherein said electrolyte is an electrolyte solution and wherein said focusing chamber includes two side walls constructed of a rigid, inert insulating material and end walls of said focusing chamber constructed of a material which is permeable to small electrolytes of said electrolyte solution and impermeable to the larger amphoteric species to be resolved in the focusing chamber.

6. An apparatus according to claim 5 wherein the side walls extend above the level of electrolyte in said reservoir.

7. An apparatus according to claim 4 wherein said focusing chamber includes two side walls constructed of semi-permeable ion-selective membranes permitting electrolytes of only one charge to pass therethrough.

8. An apparatus according to claim 7 wherein the electrode pairs are on the inside of said side walls.

9. An apparatus according to claim 7 wherein the electrode pairs are on the outside of said side walls.

10. An apparatus according to claim 4 wherein said reservoir chamber includes means for reducing the amount of current flowing through said reservoir chamber by reducing the cross-sectional area of the reservoir chamber.

11. An apparatus to claim 10 wherein said means are baffles.

12. An apparatus according to claim 4 wherein two electrodes are disposed in said reservoir chamber external to the focusing chamber whereby the flux of ions into and out of the focusing chamber is controlled by said two electrodes.

13. An process for establishing an ion concentration gradient in an electrolyte solution containing two or more types of ions which comprises: confining an electrolyte solution in a continuous focusing chamber having a long axis having an anode end and a cathode end; establishing an electric current through said solution; and providing a plurality of parallel, vertically aligned, spaced-apart electrode pairs with the members of each pair situated on opposite sides of said focusing chamber and bordering said focusing chamber such that the plane formed between each pair is orthogonal to the long axis of the focusing chamber, and applying a non-linear voltage gradient along the length of the focusing chamber by means of said electrode pairs wherein the lines of electric force have a net component parallel to the long axis of the focusing chamber, whereby the ionic species present in said electrolyte will be concentrated at either the anode or cathode end thereby establishing a steady-state pH gradient in said focusing chamber proportional to the voltage gradient.

14. A process according to claim 13 wherein the electrode spacing is non-linear.

15. A process according to claim 13 wherein the electrode spacing is linear.

16. A process according to claim 13 including providing a reservoir of electrolyte outside of the electrolyte solution in said focusing chamber communicating with the electrolyte solution in said focusing chamber.

17. A process according to claim 16 including the step of reducing the amount of current flowing through said reservoir by reducing the cross-sectional area of said reservoir.

18. An process according to claim 13 wherein amphoteric species having isoelectric focusing points are introduced into said focusing chamber in order to achieve separation of said amphoteric species on the basis of their isoelectric focusing points.

* * * * *